(12) United States Patent
Wang et al.

(10) Patent No.: US 7,550,301 B2
(45) Date of Patent: Jun. 23, 2009

(54) MALDI ANALYSIS BASED ON DERIVATIZED MATRICES FORMING COVALENT BONDS WITH ANALYTE MOLECULES

(76) Inventors: Tianxin Wang, 9768 Early Spring Way, Columbia, MD (US) 21046; Qun Liu, 9768 Early Spring Way, Columbia, MD (US) 21046; Shazhou Zou, 14376 Porsey Mill Rd., Glenwood, MD (US) 21738

( * ) Notice: Subject to any disclaimer, the term of this patent is extended or adjusted under 35 U.S.C. 154(b) by 868 days.

(21) Appl. No.: 10/755,986

(22) Filed: Jan. 13, 2004

(65) Prior Publication Data

US 2004/0142487 A1    Jul. 22, 2004

Related U.S. Application Data

(60) Provisional application No. 60/439,631, filed on Jan. 13, 2003.

(51) Int. Cl.
*G01N 24/00*    (2006.01)
(52) U.S. Cl. ........................................ 436/173; 436/86
(58) Field of Classification Search ...................... None
See application file for complete search history.

(56) References Cited

OTHER PUBLICATIONS

Voivodov et al. "Surface arrays of energy absorbing polymers enabling covalent attachment of biomolecules for subsequent laser-induced uncoupling/desorption", Tetrahedron Lett., 1996, v. 37, No. 32, pp. 5669-5672.*

* cited by examiner

*Primary Examiner*—Yelena G Gakh

(57) ABSTRACT

Methods and compounds are provided to improve the desorption and ionization of analyte for mass spectrometry analysis. More specifically, it is for laser desorption/ionization mass spectrometry. The method uses photon energy absorbing molecules that can bind with analyte either temporarily or permanently to improve the desorption and ionization of analyte.

9 Claims, 2 Drawing Sheets

MALDI ANALYSIS BASED ON DERIVATIZED MATRICES FORMING COVALENT BONDS WITH ANALYTE MOLECULES

The present application claims priority under 35 U.S.C. § 119(e) to U.S. Provisional Application No. 60/439,631, filed on Jan. 13, 2003, which provisional application is hereby incorporated by reference in its entirety.

BACKGROUND OF THE INVENTION

1. Field of the Invention

This invention relates to methods and compounds to improve the desorption and ionization of analyte for mass spectrometry analysis. More specifically, this invention relates to the field of mass spectrometry, especially to the type of matrix-assisted laser desorption/ionization used to analyze macromolecules, such as proteins or biomolecules. Most specifically, this invention relates to the method of using photon energy absorbing molecules that can bind with analyte either temporarily or permanently to improve the desorption and ionization of analyte.

2. Background Information

This invention relates generally to methods and compounds for desorption and ionization of analytes for the purpose of subsequent scientific analysis by such methods, for example, as mass spectrometry (MS) or biosensors. Generally, analysis by mass spectrometry involves vaporization and ionization of a small sample of material, using a high energy source, such as a laser, including a laser beam. Certain molecules that can absorb the photon energy of laser beam can be added to the sample to aid the desorption and ionization of analytes. These photon absorbing molecules are called matrix. The material is vaporized from the surface of a probe tip into the gas or vapor phase by the laser beam, and, in the process, some of the individual molecules are ionized. The positively or negatively charged ionized molecules are then accelerated through a short high voltage field and let fly (drift) preferably into a high vacuum chamber, at the far end of which they strike a sensitive detector. In some mass spectrometry method, such as ion mobility spectrometry, atmosphere pressure instead of high vacuum is used. Since the time-of-flight is a function of the mass of the ionized molecule, the elapsed time between ionization and impact can be used to determine the molecule's mass which, in turn, can be used to identify the presence or absence of known molecules of specific mass. Besides using time-of-flight, other methods such as ion trap also can be used to detect the mass and intensity of ion. Matrix-assisted laser desorption/ionization (MALDI) mass spectrometry has become a very important tool of modern chemistry and biotechnology. It is highly desirable that certain analyte molecules can be selectively desorbed and ionized to reduce signal peak interference and improve detection sensitivity.

A patent search was conducted to examine the means for reducing signal peak interference and improved detection sensitivity for mass spectrometry. The following prior art patents were located in the course of the patent search, and are considered to be the references most pertinent to the invention.

The Nelson U.S. Pat. No. 6,093,541, issued on Jul. 25, 2000 illustrates a Mass spectrometer having a derivatized sample presentation apparatus;

The Nelson U.S. Pat. No. 6,316,266 issued on Nov. 13, 2001 illustrates a sample presentation apparatus for mass spectrometry;

The Hutchens U.S. Pat. No. 5,719,060 issued on Feb. 17, 1998 illustrates methods and apparatus for desorption and ionization of analytes for the purpose of subsequent scientific analysis by such methods;

The Giese; Roger U.S. Pat. No. 5,952,654 issued on Sep. 14, 1999 illustrates a field-release mass spectrometry methods of releasing and analyzing substrates such as DNA;

All the prior art patents examined involve modifying the sample presentation probe to selectively bind with certain analyte molecules and washing away the unbound analyte for improved detection. None of the prior art patents used modified matrix that can selectively form covalent or non-covalent interaction with certain analyte to improve their desorption and ionization. These methods involves heterogeneous binding, intensive washing, therefore are labor intensive, time consuming and may result in loss of analytes. They improve the detection of desired analyte indirectly by washing away interference molecules in the sample to decrease the noise and can not directly increase the desorption and ionization of desired analyte. The method in our invention is primarily directed towards direct increasing the desorption and ionization of desired analyte by forming a photon energy absorbing molecules-desired analyte complex for mass spectrometry analysis.

SUMMARY OF THE INVENTION

An object of the invention is to provide improved methods and materials for desorption and ionization of multiple or selected analytes into the gas (vapor) phase.

Another object is to provide means to selectively enhance the desorption/ionization of analyte molecules by using photon energy absorbing molecules that carry certain affinity groups.

A further object is to provide means to selectively enhance the desorption/ionization of analyte molecules by using photon energy absorbing molecules that carry certain reactive groups.

Other and further objects, features and advantages will be apparent and the invention will be more readily understood from a reading of the following specification and by reference to the accompanying drawings forming a part thereof, wherein the examples of the present preferred embodiments of the invention are given for the purposes of disclosure.

DESCRIPTION OF THE INVENTIONS AND THE PREFERRED EMBODIMENT

Figure 1:
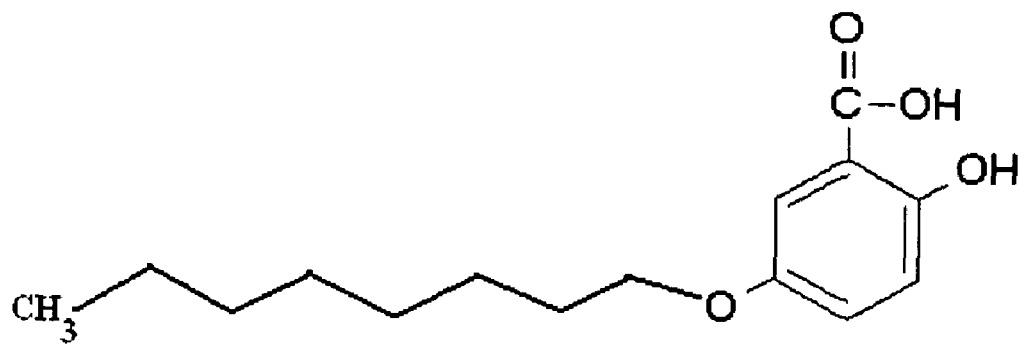
FIG. 1 shows an example of the selective affinity matrix.

Matrix for MALDI Mass (Matrix-assisted laser desorption/ionization mass spectrometry) is photon energy-absorbing molecules that can absorb energy from laser pulse and then push the analyte nearby into gas phase for mass analysis. Currently, most matrix molecules are small organic molecule such as DHB (2,5-dihydroxy benzoic acid) and sinapinic acid, which cannot selectively desorb/ionize molecules from a complex mixture of analytes. These matrix molecules also can not selectively bind with analyte either covalently or non-covalently. To perform the mass spectrometry analysis, matrix is mixed with the sample containing analyte and then added onto the probe; the probe is then inserted into the MALDI mass spectrometer for the analysis.

In our invention, photon energy absorbing molecules that can bind with certain analyte either temporarily or permanently are added to the sample solution to form a analyte-photon energy absorbing molecules complex during mixing and incubation; the resulting solution is then added onto the probe and the probe is inserted into the MALDI mass spectrometer for analysis. This kind of photon energy absorbing molecules are essentially matrix that can bind with analyte covalently or non-covalently, therefore are called binding matrix. These binding matrix molecules comprise two parts conjugated together: a photon energy absorbing motif and a binding motif. Alternatively, a carrier motif is used to connect the photon energy absorbing motif and the binding motif. The carrier can be a polymer or any other chemical entity can be used as a carrier as long as it has multiple functional groups that allow direct or indirect conjugation of the photon energy absorbing motif and the binding motif. Appropriate natural or synthetic polymers include, but are not limited to, oligomers (such as peptides), linear or cross linked polymers (such as polylysine, polyacrylic acid, proteins) or highly branched macromolecules (such as dendrimers). The photon energy absorbing motif can be matrix currently used or any other chemical entities that have strong photon energy absorbing capability. More than one photon energy absorbing unit and more than one binding unit can be incorporated in one unit of the binding matrix.

The binding could be either reactivity based covalent binding or affinity based non-covalent binding. Because matrix molecules absorb and transfer the energy to the molecules adjacent to them, selective binding of analytes to the matrix molecules can selectively desorb/ionize the analytes.

For non-covalent binding, the binding motifs are chemical entities with affinity groups having affinity for the analyte to be detected. The affinity group or groups can be any chemical or biological functionality with affinity for certain analytes. They include, but are not limited to, DNA, PNA (peptide nucleic acid), polynucleotides, antibody, antigen, aptamers, chelator, metals, lipophilic molecules, hydrophilic molecules, ionic molecules (such as acidic and basic molecules), dendrimer, polymers having affinity groups and other structures having specific interactions with certain analytes. Through the binding between the affinity groups and the analytes, the non-covalent interaction between the matrix and the specific analytes will enable the matrix selectively desorb/ionize these analytes for mass analysis.

The resulting mass detected could either be the mass of the analyte or the mass of analyte plus matrix based on the strength of the affinity. These novel matrix molecules could be used either alone or in combination with known matrix. This new method is useful in both single analyte detection and analytes pattern profiling such as protein pattern profiling for diagnosis, biomarker discovery and proteomic study. If multiple these kind of affinity matrix molecules are used for a sample containing multiple analytes, multiple analytes can be selectively detected simultaneously. Compared with other protein chip technologies and MALDI methods, this method provides a more sensitive and convenient solution.

For covalent binding, the binding motif can be any chemical entities having certain reactive groups that can covalently couple to the analyte to be detected upon incubation, therefore these binding matrix molecules are indeed reactive matrix. The reactive groups include, but are not limited to, anhydride, active ester, aldehyde, alkyl halide, acid chloride, and other reactive groups that can react with functional group such as amine, hydroxyl, SH or other groups on the analyte molecules. Upon mixing them together, the analyte molecules are covalently coupled with these reactive groups attached to the reactive matrix, and the masses detected are those of the adducts formed by the analyte molecules and the matrix. The desorption/ionization of certain molecules can thus be enhanced, and the mass spectra will exhibit a unique pattern of mass of derivatives which gives clues to structure of the molecules. These novel matrix molecules can be used either alone or in combination with known matrix.

Alternatively, pseudo-reactive matrix molecules can also be employed. A pseudo-matrix molecule is not a matrix by it self and can not absorb photon energy. It has a reactive group such as anhydride, aldehyde, alkyl halide, acid chloride, and other reactive groups that can react with functional group such as amine, hydroxyl, SH or other groups on the analyte molecules. When its reactive group reacts with a functional group and form a covalent bond, the pseudo-matrix molecule becomes capable of absorbing photon energy and performing desorption/ionization activity.

EXAMPLE 1

A DHB like molecule (photon absorbing motif) is coupled with a lipophilic long alkyl chain (affinity motif), therefore has affinity for lipophilic compounds (FIG. 1). This affinity matrix could selectively desorb/ionize lipophilic analyte for MALDI mass analysis. Using this affinity matrix as matrix and standard MALDI analysis protocol (protocol available from Mass Spectrometry for Biotechnology; Gary Siuzdak, Academic Press 1996), a sample containing a mixture of dynorphin A-(1-11) and more lipophilic acetylated dynorphin A-(1-11) at 1:1 ratio gave 10 times higher peak of acetylated dynorphin A-(1-11) than the peak of less lipophilic dynorphin A-(1-11) while using DHB as matrix gave almost same peak height for two analytes. This enhanced signal of acetylated dynorphin A-(1-11) indicates the selective desorption/ionization capability of the lipophilic affinity matrix. The typical mixing and incubation time is several minutes. Longer incubation time can result in more complete binding. The affinity motif is not limited to alkyl chain, for example, if the affinity motif is biotin instead of the long alkyl chain, the resulting affinity matrix can be used to selectively desorb/ionize avidin or streptavidin.

EXAMPLE 2

Figure 2:
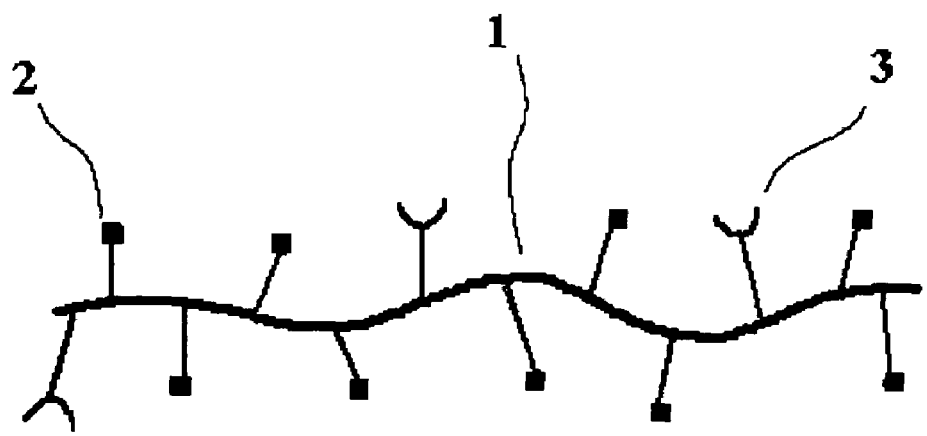
FIG. 2 shows another example of the polymer based selective affinity matrix.

FIG. 2 shows a polymer having both affinity groups and photon energy absorbing groups covalently coupled with it. The polymer 1 is polylysine (MW=20,000), the photon energy absorbing groups 2 are α-Cyano-4-hydroxycinnamic acid (CCA) molecules and the affinity groups 3 are antibodies. The CCA and antibodies are coupled to the side chains of polylysine via amide bonds. The preferred ratio of antibody to CCA is 1:5 to 1:20. This polymer can be used as a selective affinity matrix to selectively desorb/ionize the corresponding antigen in MALDI analysis. A further modification of this affinity matrix is that the affinity groups are covalently linked to the polymer back bone while the photon energy absorbing groups are bounded to the polymer by non-covalent interaction such as ion pairing or lipophilic interaction.

EXAMPLE 3

Figure 3:
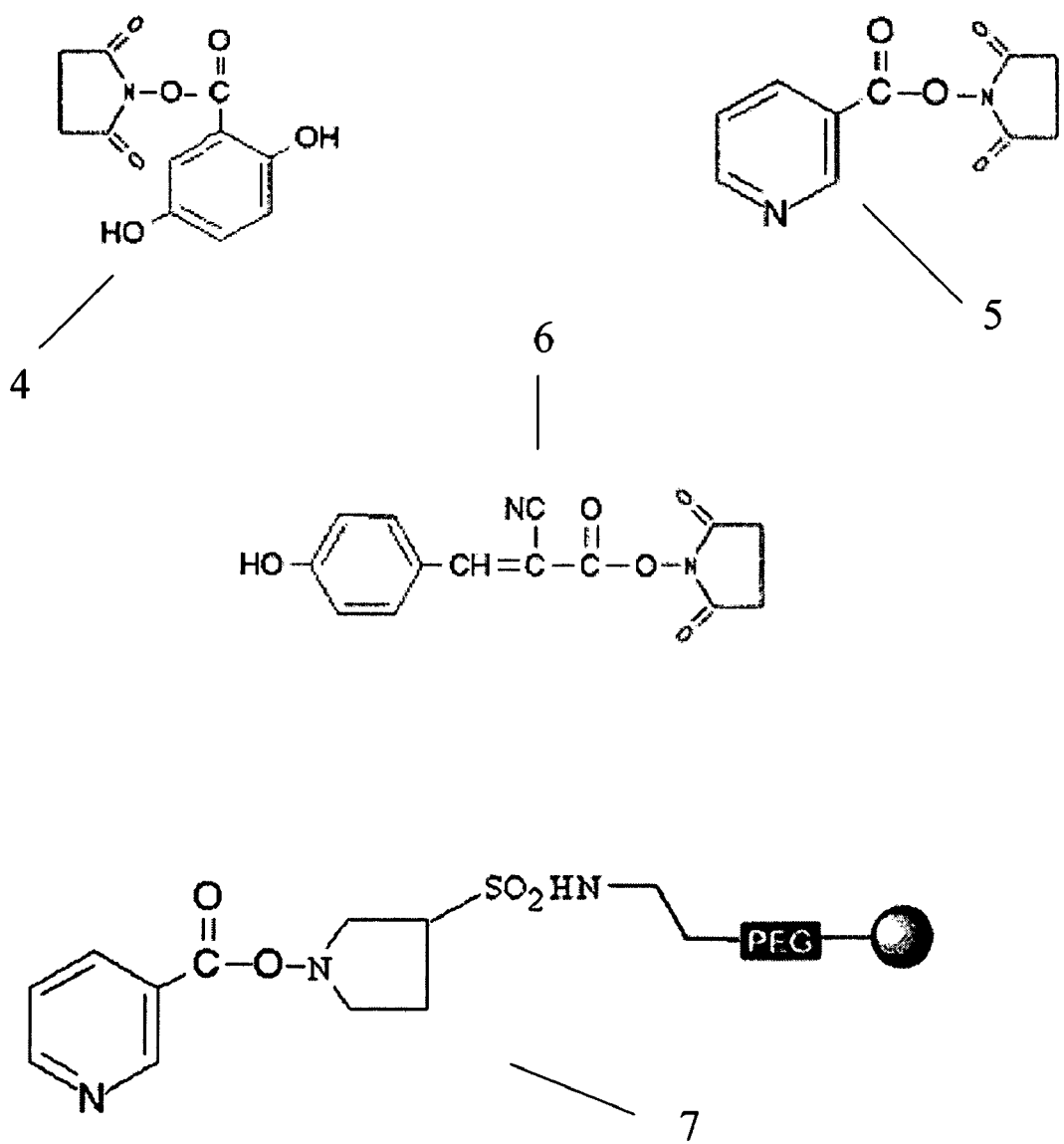
FIG. 3 shows examples of reactive matrix.

FIG. 3 shows the examples of several reactive matrix molecules: 2,5-Dihydroxybenzoic acid (DHB)-NHS ester, α-Cyano-4-hydroxycinnamic acid (CCA)-NHS ester and 3-Picolinic acid-NHS ester. The DHB-NHS ester 4, 3-Picolinic acid-NHS ester 5 and CCA-NHS ester 6 are active esters of known matrix DHB, CCA and 3-Picolinic acid respectively. They can react with the analyte molecules containing free amine groups upon mixing and incubation in sample solution. Preferred incubation time is 10~60 minutes. Using these reactive matrix molecules as matrix and standard MALDI analysis protocol, the analyte containing amine groups can be readily detected in MALDI analysis. Reactive matrix can also be immobilized on solid phase support such as the structure 7 in the figure, in structure 7, the 4, 3-Picolinic acid-NHS ester is immobilized on a PEG resin (Nova biochem), therefore allow easy purification of unreacted matrix.

All patents and publications mentioned in this specification are indicative of the level of those skilled in the art to which the invention pertains. All patents and publications are herein incorporated by reference to the same extent as if each individual publication was specifically and individually indicated to be incorporated by reference. The inventions described above involve many well known chemistry, instruments, methods and skills. A skilled person can easily find these knowledge from text books such as the chemistry textbooks, scientific journal papers and other well known reference sources.

One skilled in the art will readily appreciate that the present invention is well adapted to carry out the objects and obtain the ends and advantages mentioned, as well as those inherent therein. The compounds, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims.

What is claimed is:

1. A method for MALDI mass spectrometric analysis of analyte molecules comprising an amino group, comprising:
    providing a photon energy absorbing molecule selected from the group consisting of N-hydroxy succinimide (NHS) ester of 2,5-dihydroxybenzoic acid, alpha-cyano-4-hydroxycinnamic acid and 3-picolinic acid;
    mixing and incubating said photon energy absorbing molecule with a sample solution containing said analyte molecule, thereby forming a covalent bond between said analyte molecule and said photon energy absorbing molecule and thus forming a new molecule;
    exposing said newly formed molecule deposited on a substrate, to a laser source to desorb the analyte molecule that has not reacted with the photon energy absorbing molecule or the newly formed molecule from said substrate; and,
    performing MALDI analysis of the analyte molecule.

2. The method according to claim 1 wherein said NHS ester is sulphated.

3. The method according to claim 1 wherein said photon energy absorbing molecules are immobilized on solid support.

4. The method according to claim 1 wherein said photon energy absorbing molecules are used in combination with additional matrix.

5. The method of claim 1, wherein the analyte molecules are selected from the group consisting of peptides, polypeptides and proteins.

6. A method for MALDI mass spectrometric analysis of analyte molecules comprising an amino group, comprising:
    providing a photon energy absorbing molecule, wherein the photon energy absorbing molecule comprises a photon energy absorbing moiety, which is a residue of an acid selected from the group consisting of 2,5-dihydroxybenzoic acid, alpha-cyano-4-hydroxycinnamic acid, and 3-picolinic acid and a reactive group selected from the group consisting of anhydride, active ester, aldehyde, alkyl halide, and acid chloride;
    mixing and incubating said photon energy absorbing molecule with a sample solution containing said analyte molecule, thereby forming a covalent bond between said analyte molecule and said photon energy absorbing molecule and thus forming a new molecule;
    exposing said newly formed molecule deposited on a substrate, to a laser source to desorb the analyte molecule that has not reacted with the photon energy absorbing molecule or the newly formed molecule from said substrate; and,
    performing MALDI analysis of the analyte molecules.

7. The method of claim 6, wherein the analyte molecules are selected from the group consisting of peptides, polypeptides and proteins.

8. The method of claim 6, wherein the photon energy absorbing molecule has a reactive group which is an active ester.

9. The method of claim 6, wherein the analyte molecules are selected from the group consisting of peptides, polypeptides and proteins.

\* \* \* \* \*